(12) United States Patent
Bui et al.

(10) Patent No.: US 8,673,284 B2
(45) Date of Patent: *Mar. 18, 2014

(54) COSMETIC COMPOSITIONS CONTAINING BLOCK COPOLYMERS, TACKIFIERS AND A SELECTIVE SOLVENT FOR HARD BLOCKS

(75) Inventors: Hy Si Bui, Piscataway, NJ (US); Shaoxiang Lu, Plainsboro, NJ (US); Francois Pradier, New York, NY (US); Ramon Mercado, Clifton, NJ (US)

(73) Assignee: L'Oreal (FR)

( * ) Notice: Subject to any disclaimer, the term of this patent is extended or adjusted under 35 U.S.C. 154(b) by 1387 days.

This patent is subject to a terminal disclaimer.

(21) Appl. No.: 11/417,986

(22) Filed: May 3, 2006

(65) Prior Publication Data

US 2007/0258925 A1    Nov. 8, 2007

(51) Int. Cl.
*A61K 8/72*     (2006.01)
*A61K 31/74*    (2006.01)
*A61K 9/00*     (2006.01)

(52) U.S. Cl.
USPC ............. 424/78.08; 424/400; 424/70.11; 424/78.02; 424/78.03

(58) Field of Classification Search
USPC ............. 424/78.08, 400, 70.11, 78.02, 78.03
See application file for complete search history.

(56) References Cited

U.S. PATENT DOCUMENTS

| | | | |
|---|---|---|---|
| 2,823,195 A | 2/1958 | Shorr et al. | |
| 2,823,218 A | 2/1958 | Speier et al. | |
| 3,723,566 A | 3/1973 | Thompson et al. | |
| 4,116,924 A * | 9/1978 | Peabody | 524/270 |
| 4,164,563 A | 8/1979 | Chang | |
| 4,322,400 A | 3/1982 | Yuhas | |
| 4,369,284 A | 1/1983 | Chen | |
| 4,492,428 A | 1/1985 | Levy | |
| 4,822,852 A | 4/1989 | Wittmann et al. | |
| 4,913,235 A | 4/1990 | Harris et al. | |
| 4,976,961 A | 12/1990 | Norbury et al. | |
| 5,221,534 A | 6/1993 | Deslauriers et al. | |
| 5,262,505 A | 11/1993 | Nakashima et al. | |
| 5,272,241 A | 12/1993 | Lucarelli et al. | |
| 5,294,438 A | 3/1994 | Chang et al. | |
| 5,407,986 A | 4/1995 | Furukawa et al. | |
| 5,412,004 A | 5/1995 | Tachibana et al. | |
| 5,473,041 A | 12/1995 | Itoh | |
| 5,567,428 A | 10/1996 | Hughes | |
| 5,618,883 A | 4/1997 | Plamthottam et al. | |
| 5,648,066 A | 7/1997 | Stepniewski | |
| 5,653,968 A | 8/1997 | Carballada et al. | |
| 5,656,286 A * | 8/1997 | Miranda et al. | 424/449 |
| 5,690,918 A * | 11/1997 | Jacks et al. | 424/64 |
| 5,725,882 A | 3/1998 | Kumar et al. | |
| 5,726,220 A * | 3/1998 | Tokushige et al. | 523/125 |
| 5,756,082 A | 5/1998 | Cashin | |
| 5,837,223 A | 11/1998 | Barone et al. | |
| 5,843,407 A * | 12/1998 | El-Nokaly et al. | 424/64 |
| 5,948,393 A | 9/1999 | Tomomasa et al. | |
| 5,959,009 A | 9/1999 | Konik et al. | |
| 5,969,172 A | 10/1999 | Nye | |
| 5,985,297 A | 11/1999 | Mellul et al. | |
| 6,060,072 A | 5/2000 | Konik et al. | |
| 6,083,516 A | 7/2000 | Curtis et al. | |
| 6,103,250 A | 8/2000 | Brieva et al. | |
| 6,114,424 A | 9/2000 | Lahanas | |
| 6,177,091 B1 | 1/2001 | Bara et al. | |
| 6,200,581 B1 | 3/2001 | Lin et al. | |
| 6,248,339 B1 | 6/2001 | Knitowski et al. | |
| 6,258,347 B1 | 7/2001 | Sakuta et al. | |
| 6,267,951 B1 | 7/2001 | Shah et al. | |
| 6,309,629 B1 | 10/2001 | Travkina et al. | |
| 6,340,467 B1 | 1/2002 | Morrison | |
| 6,348,152 B1 | 2/2002 | Kawahara et al. | |
| 6,353,076 B1 | 3/2002 | Barr et al. | |
| 6,362,287 B1 | 3/2002 | Chorvath et al. | |
| 6,362,288 B1 | 3/2002 | Brewer et al. | |
| 6,376,078 B1 | 4/2002 | Inokuchi | |
| 6,387,358 B2 | 5/2002 | Chuah et al. | |
| 6,403,070 B1 | 6/2002 | Pataut et al. | |
| 6,423,324 B1 | 7/2002 | Murphy et al. | |
| 6,426,062 B1 | 7/2002 | Chopra et al. | |
| 6,433,163 B1 | 8/2002 | Ho | |
| 6,451,295 B1 | 9/2002 | Cai et al. | |
| 6,503,491 B2 * | 1/2003 | Guenin et al. | 424/65 |
| 6,517,818 B1 * | 2/2003 | Golz-Berner et al. | 424/64 |

(Continued)

FOREIGN PATENT DOCUMENTS

| CA | 2278685 | 8/1998 |
|---|---|---|
| CN | 1246787 A | 3/2000 |

(Continued)

OTHER PUBLICATIONS

Zhang et al., J. Colloid Interface Science, 2003, 266, 339-345.*
Hansen, Paint and Coating Testing Manual, 1995, Joseph V. Koleske Editor., pp. 383-404.*
European Search Report as received in corresponding European application No. 07008772.1 Feb. 18, 2008.
European Communication dated Apr. 24, 2008 as received in corresponding European application No. 07008772.1.
Co-pending U.S. Appl. No. 11/485,347 Title: Lip makeup composition with good staying power comprising a low molecular weight resin filed Jul. 13, 2006.
Co-pending U.S. Appl. No. 11/485,283—Title: Two-coat cosmetic product, uses thereof and makeup kit containing this product filed Jul. 13, 2006.
Co-pending U.S. Appl. No. PCT/US06/26310 Title: Cosmetic Compositions Containing Liposoluble Polymers and Tackifiers—PCT Filing Date: Jul. 7, 2006.
Co-pending U.S. Appl. No. 11/219,946 Title: Cosmetic compositions containing block copolymers, tackifiers and phenylated silicones— filed Sep. 6, 2005.

(Continued)

*Primary Examiner* — Abigail Fisher
(74) *Attorney, Agent, or Firm* — Lerner, David, Littenberg, Krumholz & Mentlik, LLP

(57) ABSTRACT

A cosmetic composition containing at least one block copolymer having at least one hard segment and at least one soft segment, at least one tackifier component, at least one solvent capable of solubilizing the at least one hard segment, and optionally, at least one colorant, and wherein the at least one hard segment has a $T_g$ value of about 50° C. or more and the at least one soft segment has a $T_g$ value of about 20° C. or less.

29 Claims, No Drawings

(56) References Cited

U.S. PATENT DOCUMENTS

| | | | |
|---|---|---|---|
| 6,524,598 B2 | 2/2003 | Sunkel et al. | |
| 6,541,017 B1 | 4/2003 | Lemann et al. | |
| 6,544,642 B2 | 4/2003 | Cinelli et al. | |
| 6,566,026 B2 * | 5/2003 | Watanabe et al. | 430/110.1 |
| 6,656,458 B1 | 12/2003 | Philippe et al. | |
| 6,682,748 B1 | 1/2004 | De La Poterie et al. | |
| 6,737,048 B2 * | 5/2004 | Abend et al. | 424/65 |
| 6,916,464 B2 | 7/2005 | Hansenne et al. | |
| 6,958,155 B2 | 10/2005 | Lu et al. | |
| 6,960,339 B1 | 11/2005 | Ferrari | |
| 7,078,026 B2 | 7/2006 | Ferrari et al. | |
| 7,083,800 B1 | 8/2006 | Terren et al. | |
| 7,321,011 B2 | 1/2008 | Lu et al. | |
| 7,329,699 B2 | 2/2008 | Liew et al. | |
| 7,884,158 B2 * | 2/2011 | Bui et al. | 525/64 |
| 7,887,786 B2 | 2/2011 | Tournilhac et al. | |
| 2002/0028223 A1 | 3/2002 | Vatter et al. | |
| 2002/0031968 A1 | 3/2002 | Hamaguchi et al. | |
| 2002/0048557 A1 | 4/2002 | Cai et al. | |
| 2002/0051758 A1 | 5/2002 | Cai et al. | |
| 2002/0114773 A1 | 8/2002 | Kanji et al. | |
| 2003/0035944 A1 * | 2/2003 | Blackwell | 428/328 |
| 2003/0039620 A1 | 2/2003 | Rodriguez et al. | |
| 2003/0059448 A9 | 3/2003 | Kanji et al. | |
| 2003/0068344 A1 | 4/2003 | Ferrari et al. | |
| 2003/0068348 A1 | 4/2003 | Ferrari et al. | |
| 2003/0072730 A1 | 4/2003 | Tournilhac | |
| 2003/0082129 A1 | 5/2003 | Buckingham et al. | |
| 2003/0170188 A1 | 9/2003 | Ferrari et al. | |
| 2003/0228333 A1 | 12/2003 | Fecht et al. | |
| 2003/0232030 A1 | 12/2003 | Lu et al. | |
| 2003/0235548 A1 | 12/2003 | Lu | |
| 2003/0235553 A1 | 12/2003 | Lu et al. | |
| 2004/0001799 A1 | 1/2004 | Lu et al. | |
| 2004/0009198 A1 | 1/2004 | Bernard et al. | |
| 2004/0047884 A1 | 3/2004 | Bernard et al. | |
| 2004/0052745 A1 | 3/2004 | Bernard et al. | |
| 2004/0076594 A1 | 4/2004 | Legrand | |
| 2004/0115153 A1 | 6/2004 | Yu | |
| 2004/0115154 A1 | 6/2004 | Yu | |
| 2004/0120912 A1 | 6/2004 | Yu | |
| 2004/0126336 A1 | 7/2004 | Hansenne et al. | |
| 2004/0137028 A1 | 7/2004 | de la Poterie | |
| 2004/0197285 A1 | 10/2004 | Van Dort | |
| 2004/0223936 A1 | 11/2004 | Fecht et al. | |
| 2004/0223989 A1 | 11/2004 | Auguste et al. | |
| 2004/0234612 A1 * | 11/2004 | Blin et al. | 424/489 |
| 2005/0009989 A1 | 1/2005 | Liew et al. | |
| 2005/0020769 A1 | 1/2005 | Lu et al. | |
| 2005/0061435 A1 | 3/2005 | Everaerts et al. | |
| 2005/0089492 A1 | 4/2005 | Lu et al. | |
| 2005/0158260 A1 | 7/2005 | Ferrari et al. | |
| 2005/0228115 A1 | 10/2005 | Auguste et al. | |
| 2005/0245673 A1 | 11/2005 | Ferrari et al. | |
| 2005/0287105 A1 | 12/2005 | Blin et al. | |
| 2006/0013839 A1 | 1/2006 | Yu | |
| 2006/0029560 A1 | 2/2006 | Blin | |
| 2006/0110345 A1 | 5/2006 | Lu et al. | |
| 2006/0120983 A1 | 6/2006 | Blin et al. | |
| 2006/0193801 A1 | 8/2006 | Blin et al. | |
| 2006/0204470 A1 | 9/2006 | Tournilhac | |
| 2007/0014745 A1 | 1/2007 | Arnaud et al. | |
| 2007/0020205 A1 | 1/2007 | Blin et al. | |
| 2007/0041920 A1 | 2/2007 | Blin et al. | |
| 2007/0041928 A1 | 2/2007 | Chen et al. | |
| 2007/0053859 A1 | 3/2007 | Bui et al. | |
| 2007/0055014 A1 | 3/2007 | Lu et al. | |
| 2007/0149703 A1 | 6/2007 | Caprasse et al. | |
| 2007/0212317 A1 | 9/2007 | Atis et al. | |
| 2007/0258923 A1 * | 11/2007 | Bui et al. | 424/63 |
| 2007/0258924 A1 * | 11/2007 | Bui et al. | 424/64 |
| 2007/0258925 A1 | 11/2007 | Bui et al. | |
| 2007/0258932 A1 * | 11/2007 | Bui et al. | 424/70.11 |
| 2007/0258933 A1 * | 11/2007 | Bui et al. | 424/70.11 |
| 2007/0258934 A1 * | 11/2007 | Bui et al. | 424/70.11 |
| 2008/0102049 A1 | 5/2008 | McDermott | |
| 2008/0171006 A1 * | 7/2008 | Bui et al. | 424/64 |
| 2008/0171007 A1 * | 7/2008 | Bui | 424/64 |
| 2008/0171008 A1 * | 7/2008 | Bui | 424/64 |
| 2008/0254076 A1 | 10/2008 | Ferrari et al. | |
| 2010/0098648 A1 | 4/2010 | Yu | |
| 2012/0219516 A1 | 8/2012 | Ramada et al. | |

FOREIGN PATENT DOCUMENTS

| | | |
|---|---|---|
| CN | 1646656 A | 7/2005 |
| CN | 1761446 A | 4/2006 |
| EP | 0377447 A2 | 7/1990 |
| EP | 0600445 | 6/1994 |
| EP | 0682940 | 11/1995 |
| EP | 0693517 A1 | 1/1996 |
| EP | 0850649 | 7/1998 |
| EP | 0966263 | 12/1999 |
| EP | 0975320 | 2/2000 |
| EP | 1005322 | 6/2000 |
| EP | 1 582 203 A1 | 10/2005 |
| FR | 2765800 A1 | 1/1999 |
| FR | 2 785 530 | 5/2000 |
| FR | 2 842 100 | 1/2004 |
| FR | 2 873 030 | 1/2006 |
| GB | 1348783 A | 3/1974 |
| JP | 60255713 A | 12/1985 |
| JP | 2602053 | 9/1989 |
| JP | 2657219 | 10/1989 |
| JP | H06-24969 | 2/1994 |
| JP | 2000-178126 | 6/2000 |
| JP | 2001-97852 | 4/2001 |
| JP | 2001507591 A | 6/2001 |
| JP | 2001-511161 | 8/2001 |
| JP | 2002097366 A | 4/2002 |
| JP | 2002154916 | 5/2002 |
| JP | 2002-528477 | 9/2002 |
| JP | 2003516949 A | 5/2003 |
| JP | 2004-35567 | 2/2004 |
| JP | 2004051850 | 2/2004 |
| JP | 2004-115774 | 4/2004 |
| JP | 2004256539 A | 9/2004 |
| JP | 2005225867 A | 8/2005 |
| JP | 2005-528471 | 9/2005 |
| JP | 2005247730 | 9/2005 |
| JP | 2006-28181 | 2/2006 |
| JP | 2007297391 A | 11/2007 |
| JP | 2007532754 A | 11/2007 |
| JP | 2008512498 A | 4/2008 |
| JP | 2009-521549 | 6/2009 |
| KR | 9002521 | 4/1990 |
| WO | 9736573 A1 | 10/1997 |
| WO | 98/34588 | 8/1998 |
| WO | 0109239 A1 | 2/2001 |
| WO | 03087254 A2 | 10/2003 |
| WO | 2003087254 A | 10/2003 |
| WO | 2004/066918 | 8/2004 |
| WO | WO 2007/008575 A1 | 1/2007 |
| WO | WO 2007/015166 A3 | 2/2007 |
| WO | 2007031872 A2 | 3/2007 |
| WO | WO 2007/031872 A2 | 3/2007 |
| WO | 2007/078825 | 7/2007 |

OTHER PUBLICATIONS

Co-pending U.S. Appl. No. 11/417,974 Title: Cosmetic compositions containing block copolymers, tackifiers and a selective solvent for soft blocks—filed May 3, 2006.

Co-pending U.S. Appl. No. 11/417,975 Title: Cosmetic compositions containing block copolymers, tackifiers and a solvent mixture—filed May 3, 2006.

Co-pending U.S. Appl. No. 11/417,981 Title: Cosmetic compositions containing block copolymers, tackifiers and modified silicones—filed May 3, 2006.

Co-pending U.S. Appl. No. 11/417,977 Title: Cosmetic compositions containing block copolymers, tackifiers and shine enhancing agents—filed May 3, 2006.

Co-pending U.S. Appl. No. 11/418,327 Title: Cosmetic compositions containing block copolymers, tackifiers and gelling agents—filed May 3, 2006.

(56) References Cited

OTHER PUBLICATIONS

Chinese Communication dated May 15, 2009 as received in corresponding Chinese application No. 200710128891.9.
J. Bandrup and E.H. Immergut, Solubility Parameter ValueS, Polymer Handbook, 1989, pp. 519-559, 3rd edition, Published by Wiley-Interscience Publication, Canada.
C. M. Hansen, The Three Dimensional Solubility Parameter—Key to Paint Component Affinities: I. Solvents, Plasticizers, Polymers, and Resins, Journal of Paint Technology, 1967, pp. 104-117, vol. 39, No. 505, Published by Federation of Societies for Paint Technology.
J. Wenninger and G.N. McEwen, Jr., International Cosmetic Ingredient Dictionary, 1995, 6th edition, vol. 1 & 2, Published by the Cosmetic, Toiletry, and Fragrance Association, Washington, DC.
Japanese Communication dated Nov. 17, 2009 as received in corresponding Japanese Application No. 2007-121914.
Japanese Communication dated Mar. 1, 2011 as received in corresponding Japanese Application No. 2007-121914.
Chinese Communication dated Nov. 17, 2010 as received in corresponding Chinese application No. 200710128891.9 4.
Factsheet—DOW Corning 670 Fluid-Intellectual Property Statement—Apr. 14, 2005.
Virginie Caprasse, Isabelle Van Reeth, DOW Corning S.A., Research Disclosure, A new silicone resin for personal care applications, Research Disclosure Database No. 486008, Published in Oct. 2004 (Eiectronic publication date: Sep. 10, 2004 ), Research Disclosure Journal, Kenneth Mason Publications Ud., The Book Barn, Westbourne, Hants. P010 8RS UK.
Chinese Communication dated May 8, 2009 as received in corresponding Chinese application No. 200710128890.4.
Chinese Communication dated May 9, 2011 as received in corresponding Chinese application No. 200710128890.4.
European Communication dated Mar. 31, 2008 as received in corresponding European application No. 07008771.3.
Japanese Communication dated Mar. 1, 2011 as received in corresponding Japanese application No. 2007-121913.
Japanese Communication dated Nov. 17, 2009 as received in corresponding Japanese application No. 2007-121913.
Silkflo Technical Sheet, http://www.in-cosmeticsasia.com/Exhibitorlibrary/205/Sellsheet_-Silkflo_new_Aug07 2.pdf, obtained online on Sep. 2, 2009.

* cited by examiner

COSMETIC COMPOSITIONS CONTAINING BLOCK COPOLYMERS, TACKIFIERS AND A SELECTIVE SOLVENT FOR HARD BLOCKS

BACKGROUND OF THE INVENTION

There have been many developments in connection with improving comfort, wear, shine and/or longevity of cosmetic compositions for the face, eye, lips nails or hair. Commercially available lip treatment compositions such as lip glosses and lipsticks possess a certain level of gloss or shine depending of their composition. Efforts have been made through the use of high refractive index fluids to further enhance the shine or gloss of such products, but the wear of gloss or shine is limited. Moreover, these lip treatment compositions are tacky and uncomfortable to apply due, oftentimes, to the presence of high molecular weight polymers having a high viscosity which are used to maintain the wear of shine/gloss.

While other efforts to improve shine/gloss involve the use of silicone fluids, wear of shine leaves much to be desired. Therefore, it is an object of the present invention to provide a lip treatment composition which is comfortable to apply and wear, and has long lasting shine/gloss.

BRIEF SUMMARY OF THE INVENTION

A first aspect of the present invention is directed to a cosmetic composition comprising:
  (a) at least one block copolymer having at least one hard segment and at least one soft segment;
  (b) at least one tackifier component;
  (c) at least one solvent capable of solubilizing the at least one hard segment; and
  (d) optionally, at least one colorant,
wherein the at least one hard segment has a $T_g$ value of 50° C. or more, the at least one soft segment has a $T_g$ value of 20° C. or less.

A second aspect of the present invention is directed to a method of treating lips by contacting the lips with the above-disclosed cosmetic composition.

DETAILED DESCRIPTION OF THE INVENTION

Other than in the operating examples, or where otherwise indicated, all numbers expressing quantities of ingredients and/or reaction conditions are to be understood as being modified in all instances by the term "about".

The physical and rheological properties of block copolymers can be controlled by using specific types of solvents capable of solubilizing the hard and/or soft block segments. A solvent capable of solubilizing the soft segment causes the block copolymer to possess a morphology and rheology different from that obtained using a solvent capable of solubilizing the hard segment. Similarly, the physical properties of a block copolymer solution based on a mixture of solvents capable of solubilizing both hard and soft segments are different from those obtained when using solvents capable of solubilizing only the soft segments or solvents capable of solubilizing only the hard segments.

It has been surprisingly discovered that a lip treatment composition containing: (a) a block copolymer having at least one hard segment and at least one soft segment, (b) a tackifier, and (c) at least one solvent capable of solubilizing the at least one hard segment of the block copolymer, can deliver a comfortable, long lasting shine or gloss when applied onto lips.

Block Copolymers

The block copolymers of the present invention are characterized by the presence of at least one "hard" segment, and at least one "soft" segment. Aside from their compositional nature, the hard and soft segments of the block copolymers of the present invention are defined in terms of their respective glass transition temperatures, "$T_g$." More particularly, the hard segment has a $T_g$ of 50° C. or more, whereas the soft segment has a $T_g$ of 20° C. or less. The glass transition temperature $T_g$ for the hard block can range from 50° C. to 150° C.; 60° C. to 125° C.; 70° C. to 120° C.; 80° C. to 110° C. The glass transition temperature $T_g$ for the soft segment of the block copolymer can range from 20° C. to –150° C.; 0° C. to –135° C.; –10° C. to –125° C.; –25° C. to –100° C. A more in depth explanation can be found in U.S. Pat. Nos. 5,294,438 and 6,403,070, the entire contents of which are hereby incorporated by reference.

One type of block copolymer which may be employed by the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In some embodiments, the thermoplastic elastomer of the present invention may be chosen from the class of KRATON™ rubbers (Shell Chemical Company) or from similar thermoplastic elastomers. KRATON™ rubbers are thermoplastic elastomers in which the polymer chains comprise a di-block, tri-block, multi-block or radial or star block configuration or numerous mixtures thereof. The KRATON™ tri-block rubbers have polystyrene (hard) segments on each end of a rubber (soft) segment, while the KRATON™ di-block rubbers have a polystyrene (hard) segment attached to a rubber (soft) segment. The KRATON™ radial or star configuration may be a four-point or other multipoint star made of rubber with a polystyrene segment attached to each end of a rubber segment. The configuration of each of the KRATON™ rubbers forms separate polystyrene and rubber domains.

Each molecule of KRATON™ rubber is said to comprise block segments of styrene monomer units and rubber monomer and/or co-monomer units. The most common structure for the KRATON™ triblock copolymer is the linear A-B-A block type styrene-butadiene-styrene, styrene-isoprene-styrene, styrene-ethylenepropylene-styrene, or styrene-ethylenebutylene-styrene. The KRATON™ di-block is preferably the AB block type such as styrene-ethylenepropylene, styrene-ethylenebutylene, styrene-butadiene, or styrene-isoprene. The KRATON™ rubber configuration is well known in the art and any block copolymer elastomer with a similar configuration is within the practice of the invention. Other block copolymers are sold under the tradename SEPTON (which represent elastomers known as SEEPS (styrene ethylene/ethylene-propylene-styrene), sold by Kurary, Co., Ltd) and those sold by Exxon Dow under the tradename VECTOR™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymers enhances the integrity of the film formed. The gel may also be transparent, translucent or opaque, depending upon the other cosmetically acceptable ingredients added, as described herein.

It is preferred that the styrene content of the block copolymer be less than 30% by weight, preferably less than 25% by weight, and more preferably less than 20% by weight, based on the weight of the block copolymer. This is because of the tendency of block copolymers having a styrene content of greater than 30% by weight to harden/gel in conventional carrier systems. However, in the event that a block copolymer having a styrene content of greater than 30% by weight is used, it may be necessary to also employ a co-solvent or functional ingredient capable of dissolving a styrene block in an amount effective to control the hardening/gelling of the styrene-containing elastomer in the cosmetic composition.

A particularly preferred block copolymer for use in the present invention is a combination of di-block and tri-block copolymers of styrene-ethylene/butylene-styrene, commercially available from Shell Chemical Company under trade name KRATON G1657M. It should be noted, however, that any thermoplastic elastomer of the block copolymer type having at least one soft and at least one hard segment may be used without departing from the spirit of the invention.

The block copolymer is generally present in the cosmetic composition in an amount ranging from greater than 0% to 50% by weight; greater than 0% to 40% by weight; greater than 0% to 30% by weight; greater than 0% to 20% by weight; greater than 0% to 10% by weight, based on the weight of the composition.

Tackifiers

A substance is described as a tackifier if, by adding it to a block copolymer, the resulting composition has the properties of a pressure sensitive adhesive. In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter $\delta$ according to the Hansen solubility space is defined in the article "*Solubility Parameter Values*" by Eric A. Grulke in the work "*Polymer Handbook*" 3rd edition, Chapter VII, pages 519-559, the entire content of which is hereby incorporated by reference, by the relationship:

$$\delta=(d_D^2+d_P^2+d_H^2)^{1/2}, \text{ in which:}$$

$d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like). The definition of the solvents in the three-dimensional solubility space according to Hansen is given in the article by C. M. Hansen: "*The three-dimensional solubility parameters*" J. Paint Technol., 39, 105(1967), the entire content of which is hereby incorporated by reference.

The at least one tackifier used in the present invention will have a solubility parameter corresponding to $\delta$ and the block copolymer will have at least one segment whose solubility parameter corresponds to $\delta\pm2$, preferably $\delta\pm1.7$, more preferably $\delta\pm1.5$, more preferably $\delta\pm1.3$, more preferably $\delta\pm1.0$, more preferably $\delta\pm0.7$, more preferably $\delta\pm0.5$, and more preferably $\delta\pm0.3$.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar. (Non-polar meaning that the tackifier is substantially free of monomers having polar groups. Preferably, the polar groups are not present, however, if they are present, they are preferably present in an amount of up to about 5% by weight, preferably up to about 2% by weight, and more preferably up to about 0.5% by weight.)

In some embodiments, the tackifier may have a softening point (Ring and Ball, as measured by ASTM E-28) of 80° C. to 150° C., preferably 100° C. to 130° C. In other embodiments the tackifier may be liquid and have an R and B softening point of between about −70° C. and 70° C.

In some embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name REGALITE°. In other embodiments, aliphatic or aromatic hydrocarbon-based tackifying resins, for instance the resins sold under the name "PICCOTAC" and "HERCOTEC" from Hercules or "ESCOREZ" from Exxon, may also be used. It is also to be understood that mixtures of tackifiers may also be employed without departing from the spirit of the invention.

A particularly preferred tackifier for use in the present invention is a hydrogenated hydrocarbon resin such, for example, a hydrogenated styrene/methyl styrene/indene copolymer, commercially available from Eastman under the tradename REGALITE☐ R1100.

The tackifier is present in the cosmetic composition of the present invention in an amount ranging from greater than 0% to 90% by weight; greater than 0% to 70% by weight; greater than 0% to 60% by weight; greater than 0% to 50% by weight; greater than 0% to 40%; greater than 0% to 30% by weight; greater than 0% to 20% by weight, based on the weight of the composition.

Solvents

The cosmetic compositions of the present invention also contain at least one solvent capable of solubilizing the at least one hard segment of the block copolymer. Solvents which may be used herein are typically characterized in terms of their viscosity at room temperature, weight average molecular weight and solubility parameter in relation to the at least one hard segment of the block copolymer.

The solvent will have a viscosity, at room temperature, of from 1 to 200 cps, preferably from 1 to 150 cps, more preferably from 1 to 100 cps, more preferably from 2 to 60 cps, and more preferably from 2 to 40 cps.

The solvent used in the present invention will have a solubility parameter corresponding to $\delta'$ and the block copolymer will have at least one soft segment whose solubility parameter corresponds to $\delta' \pm 2$, preferably $\delta' \pm 1.7$, more preferably $\delta' \pm 1.5$, more preferably $\delta' \pm 1.3$, more preferably $\delta' \pm 1.0$, more preferably $\delta' \pm 0.7$, more preferably $\delta' \pm 0.5$, and more preferably $\delta' \pm 0.3$.

Nonvolatile solvents which can be used in the invention include, but are not limited to, monoesters, diesters, triesters, mixed aliphatic and/or aromatic, polar oils such as: hydrocarbon-based oils of animal origin, such as perhydrosqualene; hydrocarbon-based plant oils such as liquid triglycerides of fatty acids and of glycerol, in which the fatty, acids may have varied chain lengths, these chains being linear or branched, and saturated or unsaturated; these oils can be chosen, for example, from wheat germ oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quinoa oil, olive oil, rye oil, safflower oil, candlenut oil, passion flower oil, musk rose oil and caprylic/capric acid triglycerides such as those sold by the company Stéarineries Dubois or those sold under the names MIGLYOL 810, 812 and 818 by the company Dynamit Nobel; natural or synthetic esters of formula R1COOR2, wherein R1 is a higher fatty acid residue comprising 7 to 19 carbon atoms, and R2 is a branched hydrocarbon-based chain comprising 3 to 20 carbon atoms, such as, for example, purcellin oil (cetostearyl octanoate), isopropyl myristate and alkyl or polyalkyl octanoates, decanoates or ricinoleates; synthetic ethers of formula R3COR4, wherein R3 is a C3 to C19 alkyl radical, and R4 is a C3 to C20 alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctyl-cyclohexane; aromatic hydrocarbons, for example, alkenes such as benzene, toluene, 2,4-dimethyl-3-cyclohexene, dipentene, p-cymene, naphthalene or anthracene, and esters such as isostearyl benzoate; primary, secondary or tertiary amines such as triethanolamine; and mixtures thereof. In one embodiment, synthetic esters such as isopropyl myristate are used.

Preferred esters are those having a weight average molecular weight in the range of 100 to 600, preferably from 100 to 500. Examples thereof include, but are not limited to, C12-15 alkyl benzoate, isopropyl myristate (Mw=270), isopropyl palmitate (Mw=300), isononyl isononanoate, cetyl ethylhexanoate (Mw=368), neopentyl glycol diethylhexanoate (Mw=356), diisopropyl sebacate (Mw=286).

The solvent capable of solubilizing the hard segment may typically be present in the composition of the invention in an amount of from greater than 0% to 85% by weight; greater than 0% to 75% by weight; greater than 0% to 55% by weight; greater than 0% to 45% by weight; greater than 0% to 40% by weight, based on the weight of the composition.

According to a preferred embodiment of the present invention, the solvent may be mixed with at least one co-solvent having a high molecular weight and high viscosity, in order to improve the flow of the lip treatment composition during application onto the lips, as well as its feel and comfort thereon.

The high viscosity co-solvents have weight average molecular weights ranging from 500 to 4000, preferably from 500 to 3000, and more preferably from 500 to 2500. Examples thereof include, but are not limited to, capric/caprylic triglyceride (Mw=500), diisopropyl dimmer dilinoleate (Mw=644), diisostearyl fumarate (Mw=620), diisostearyl malate (Mw=640), pentaerythrityl tetraoleate, neopentyl glycol diethylhexanoate, diethylhexyl sebacate and tricaprylate/tricaprate.

These co-solvents may be employed in the composition of the invention in an amount of from greater than 0% to 60% by weight; greater than 0% to 50% by weight; greater than 0% to 40% by weight; greater than 0% to 30% by weight; greater than 0% to 25% by weight, all weights based on the weight of the composition.

In the event that at least one hard segment solvent, and at least one hard segment co-solvent are used in combination, the mixture will have a viscosity of from 20 to 5000 cps, preferably from 20 to 2000 cps, and more preferably from 20 to 1500 cps. The viscosity of the mixture is determined using the formula:

$$\eta_{mix} = \prod_{i}^{n} \eta_i^{\phi_i}$$

wherein $\eta_{mix}$ represents the viscosity of the mixture, $\eta_i$ represents the viscosity of the individual components, and $\phi_i$ represents the weight fraction of the individual components.

Colorant

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation.

Shine Enhancing Agents

It may, at times, be desirable to provide cosmetic compositions having enhanced shine/gloss properties. In those instances, at least one shine enhancing agent would be employed in the composition.

Suitable shine enhancing agents include those compounds having a refractive index ranging from 1.45 to 1.60, and a weight average molecular weight of less than 15,000, preferably less than 10,000, preferably less than 2,000. Examples thereof include, but are not limited to, phenylated silicones such as those commercialized under the trade name "ABIL AV 8853" by Goldschmidt, those commercialized under the trade names "DC 554", "DC 555", "DC 556", "SF 558" by Dow Corning; and those commercialized under the trade name "SILBIONE 70633 V 30" by Rhône-Poulenc.

Additional examples of suitable phenylated silicones include, but are not limited to, those commercialized by Wacker Silicones such as BELSIL PDM 20, a phenylated silicone with a viscosity at 25° C. of approximately 20 cSt; BELSIL PDM 200, a phenylated silicone with a viscosity at 25° C. of approximately 200 cSt; BELSIL PDM 1000, a phenylated silicone with a viscosity at 25° C. of approximately 1000 cSt.

Additional examples of suitable phenylated silicones include, but are not limited to, those commercialized by Wacker Silicones such as Belsil PDM 20, a phenylated silicone with a viscosity at 250° C. of approximately 20 cSt; Belsil PDM 200, a phenylated silicone with a viscosity at 25° C. of approximately 200 cSt; Belsil PDM 1000, a phenylated silicone with a viscosity at 25° C. of approximately 1000 cSt.

Additional examples of suitable shine enhancing agents include, but are not limited to, polycyclopentadiene, poly (propylene glycol) dibenzoate (nD=1.5345), aminopropyl phenyl trimethicone (nD=1.49-1.51), pentaerythrityl tetraoleate commercially available as PURESYN 4E68 (nD=1.473) from ExxonMobil, and PPG-3 benzyl ether myristate commercially available as CRODAMOL STS (nD=1.4696) from Croda Inc.

Particularly preferred shine enhancing agents are the phenylated silicones such as phenyl trimethicone, and trimethyl pentaphenyl trisiloxane, and esters such as pentaerythrityl tetraoleate, and PPG-3 benzyl ether myristate.

The shine enhancing agent may be present in the composition of the invention in an amount of up to 40% by weight; up to 30% by weight; up to 20% by weight; from 1 to 20% by weight; from 2 to 20% by weight, based on the weight of the composition.

Modified Silicones

The cosmetic compositions of the present invention may contain at least one modified silicone to improve the texture and comfort. Examples of suitable modified silicones include, but are not limited to, polyethyleneoxy- and/or polypropyleneoxy-modified silicone, alkoxy-modified silicone, hydroxyalkyl-modified silicone, acyloxyalkyl-modified silicone, alkyl-modified silicone, amino-modified silicone, epoxy-modified silicone, carboxyl-modified silicone, chloroalkyl-modified silicone, alkyl-higher-alcohol-ester-modified silicone, alcohol-modified silicone, polyether-modified silicone, phenyl-modified silicone, alkylpolyglyceryl-modified silicone, perfluoroalkyl polyether-co-modified silicone and fluorine-modified silicone.

The modified silicone may be present in the composition of the invention in an amount of up to 30% by weight; up to 25% by weight; up to 20% by weight; up to 10% by weight; up to 8% by weight, based on the weight of the composition.

Waxes

In some embodiments, it may be desirable to formulate cosmetic compositions in accordance with the present invention which are free of wax. However, in the event that a wax is employed, it will be present in an amount of from about 0.1% to about 30% by weight, based on the total weight of the composition. Suitable waxes are those generally used in cosmetics and dermatology. Examples thereof include, but are not limited to, those of natural origin such as beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil. Examples of suitable synthetic waxes include, but are not limited to, polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C.

Gelling Agents

The compositions of the invention may also be optionally gelled with an oil-phase gelling agent. The gelling agent increases the liquid fatty phase viscosity and leads to a solid or flowable composition when introduced in said fatty phase. The gelling agent does not encompass waxes, in the sense that it is not waxy. The at least one gelling agent may be chosen from gelling agents in polymeric form and gelling agents in mineral form. The gelling agent may be chosen from agents that gel via chemical reticulation and agents that gel via physical reticulation.

Modified clays may be used as gelling agents, examples of which include, but are not limited to, hectorites modified with an ammonium chloride of a C10 to C22 fatty acid, such as hectorite modified with distearyldimethylammonium chloride, also known as quaternium-18 bentonite, such as the products sold or made under the names BENTONE 34 by the company Rheox, CLAYTONE XL, CLAYTONE 34 and CLAYTONE 40 sold or made by the company Southern Clay, the modified clays known under the name quaternium-18 benzalkonium bentonites and sold or made under the names CLAYTONE HT, CLAYTONE GR and CLAYTONE PS by the company Southern Clay, the clays modified with stearyldimethylbenzoylammonium chloride, known as stearalkonium bentonites, such as the products sold or made under the names CLAYTONE APA and CLAYTONE AF by the company Southern Clay, and BARAGEL 24 sold or made by the company Rheox.

Other mineral gelling agents, which can be used in the invention, include silica, such as fumed silica. The fumed silica may have a particle size, which may be nanometric to micrometric, for example ranging from 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "AEROSIL 130®", "AEROSIL 200®", "AEROSIL 255®", "AEROSIL 300®" and "AEROSIL 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be: trimethylsiloxyl groups, which are obtained in particular by treating fumed silica in the presence of hexamethyldisilazane. Silicas thus treated are known as "silica silylate" according to the CTFA dictionary (6th edition, 1995). They are sold or made, for example, under the references "AEROSIL R812®" by the company Degussa and "CAB-O-SIL TS-530®" by the company Cabot; dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA dictionary (6th edition, 1995). They are sold or made, for example, under the references "AEROSIL R972®" and "AEROSIL R974®" by the company Degussa, and "CAB-O-SIL TS-610®" and "CAB-O-SIL TS-720®" by the company Cabot; groups derived from reacting fumed silica with silane alkoxides or siloxanes. These treated silicas are, for example, the products sold or made under the reference "AEROSIL R805®" by the company Degussa.

According to the invention, hydrophobic silica, such as fumed silica, may be used as a lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one lipophilic gelling agent can allow the exudation of the composition to be limited and can allow its stability to be increased, while at the same time conserving the composition's glossy appearance, which is not possible with waxes such as those used conventionally in cosmetics and dermatology.

The at least one gelling agent, if used, will typically be present in an amount of from 0.1% to 20% by weight, preferably from 0.1% to 15% by weight, and more preferably from 0.1 to 10% by weight, based on the weight of the composition.

Additives/Auxiliary Agents

The compositions of the present invention may further comprise at least one cosmetically or dermatologically acceptable additive such as a thickener, a film former, a plasticizer, an antioxidant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

While the use of a plasticizer is not necessary in the lip treatment compositions of the present invention, its use may, nevertheless, be desirable. Plasticizers are organic compounds added to a high polymer both to facilitate processing and to increase the flexibility and toughness of the final product by internal modification of the polymer molecule. Examples of suitable plasticizers include, but are not limited to, oils, cellulose esters, phthalate esters, adipate esters, sebacate esters, tricresyl phosphate, castor oil, glycol ethers, benzyl alcohol, triethyl citrate, and propylene carbonate.

Particularly preferred plasticizers include isopropyl palmitate and alkyl benzoate. A plasticizer, if used, will typically be present in an amount of from 1 to 70% by weight, preferably from 2 to 50% by weight, and more preferably from 5 to 20% by weight, based on the weight of the composition.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Mixtures of preservatives may certainly be used, e.g., the mixture of methyl-paraben, ethylparaben, propylparaben and butylparaben sold under the name NIPASTAT by Nipa, and the mixture of phenoxyethanol, methylparaben, ethylparaben, propylparaben and butylparaben sold under the name Phenonip, also by Nipa. These preservatives may be present in amounts ranging from about 0.01 to about 10% by weight, preferably from 0.5% to about 5% by weight, and more preferably from about 0.8 to about 3% by weight, based on the weight of the composition.

Fillers that may be used in the compositions of the invention include, for example, silica powder; talc; polyamide particles and especially those sold under the name ORGASOL by the company Atochem; polyethylene powders; microspheres based on acrylic copolymers, such as those based on ethylene glycol dimethacrylate/lauryl methacrylate copolymer sold by the company Dow Corning under the name POLTRAP; expanded powders such as hollow microspheres and especially the microspheres sold under the name EXPANCEL by the company Kemanord Plast or under the name MICROPEARL F 80 ED by the company Matsumoto; powders of natural organic materials such as crosslinked or noncrosslinked corn starch, wheat starch or rice starch, such as the powders of starch crosslinked with octenyl succinate anhydride, sold under the name DRY-FLO by the company National Starch; silicone resin microbeads such as those sold under the name TOSPEARL by the company Toshiba Silicone; clays (bentone, laponite, saponite, etc.) and mixtures thereof. These fillers may be present in amounts ranging from about 0.1 to about 50% by weight, preferably from 0.5 to about 30% by weight, and more preferably from about 1 to about 20% by weight, based on the weight of the composition.

The compositions of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. What is a safe and effective amount of the active ingredient will vary with the specific active agent, the ability of the active agent to penetrate through the skin, the age, health and skin condition of the user, and other like factors. Typically, the active ingredient may be present in amounts ranging from about 0.01 to about 20% by weight, preferably from 0.1 to about 10% by weight, and more preferably from about 0.5 to about 5% by weight, based on the weight of the composition.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

Anti-Acne Actives: Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Antimicrobial and Antifungal Actives: Examples of antimicrobial and antifungal actives include .beta.-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

The cosmetic compositions of this invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as PARSOL®1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

The lip treatment composition of the invention may be in the form of a lipstick, a lip gloss or a lip pencil, optionally having care or treating properties.

Rheology

The rheological properties of lip-gloss compositions in accordance with the present invention are determined by using a controlled stress rheometer, commercially available from TA Instruments under the name AR-G2. The samples are measured using a parallel plate having a stainless steel, cross hatched, 40 mm diameter plate. The gap is set at 1,000 microns. The desired temperature is precisely controlled by a Peltier system.

The lip-gloss sample is transferred to the rheometer, and heated to 35° C. for about 10 minutes. The sample is then cooled and held at 25° C. for about 10 minutes or more.

The linear viscoelastic regime is determined by oscillation stress sweep mode with a range of from 1 mN·m to 100 mN·m, at a constant frequency of 1 rad/s. Said linear viscoelastic regime corresponds to the elastic/storage modulus G', within the above range, when the elastic/storage modulus G' is constant, or nearly constant, at the applied oscillation stress.

The frequency sweep experiment is then performed from 100 rad/s to 0.01 rad/s at a low oscillation stress in the linear viscoelastic regime. The elastic/storage modulus G' at a frequency ω of 0.01 rad/s is determined from the frequency sweep mode.

The lower the value of the elastic/storage modulus G', at a frequency ω of 0.01 rad/s, the better the wetting property and the less creep resistance for the lip-gloss composition.

In the linear viscoelastic regime, the elastic/storage modulus G' at a frequency ω of 0.01 rad/s, of compositions in accordance with the present invention, is in the range of from 0.01 Pa to 500 Pa at 25° C.

After finishing the dynamic oscillation experiment, the same sample is equilibrated for 10 minutes, at a constant temperature of 25° C. Creep and recovery measurements are then performed at a constant stress of 0.8 Pa.

The creep viscosity ($\eta_{creep}$) of the lip gloss composition, measured at a constant stress (σ) of 0.8 Pa, is determined from the creep strain ($\gamma_{creep}$) and the recoverable strain ($\gamma_{recovery}$), wherein the creep strain duration ($t_{creep}$) is 10 minutes and the recoverable strain duration is 30 minutes. The creep viscosity is calculated by the following expression:

$$\eta_{creep} = \frac{\sigma t_{creep}}{(\gamma_{creep}(t=10 \text{ min}) - \gamma_{recovery}(t=30 \text{ min}))}$$

A high creep viscosity value ($\eta_{creep}$) at low stress, with a creep time of 10 minutes (near zero shear rate), provides for a longer wear of the composition. Therefore, a lip composition with a high creep viscosity value ($\eta_{creep}$) at low stress will maintain its structure, thus its stability, at rest, will show less migration, and will provide a lasting shine.

The creep viscosity ($\eta_{creep}$) of compositions in accordance with the present invention, at a constant stress (σ) of 0.8 Pa, is in the range of from 2 Pa·s to 150,000 Pa·s at 25° C.

The present invention is further described in terms of the following non-limiting example. Unless otherwise indicated, all parts and percentages are on a weight-by-weight percentage basis.

Example 1

A lip gloss composition in accordance with the present invention was prepared per the following formula:
All values are expressed in % w/w.

| PHASE | TRADE NAME | % w/w |
|---|---|---|
| A | FINSOLV TN [1] | 25.43 |
| B | KRATON G1657 M | 8.00 |
| C | REGALITE R1100 | 24.00 |
| D | PRISORINE 3631 [2] | 10.00 |
|   | CRODAMOL STS | 24.26 |
| E | TITANIUM DIOXIDE | 0.15 |
|   | IRON OXIDE | 0.13 |
|   | D&C RED NO. 7 | 0.10 |
|   | BLUE 1 LAKE | 0.01 |
|   | BLACK IRON OXIDE | 0.04 |
|   | FINSOLV TN [1] | 0.88 |
| F | MICA | 3.00 |
|   | AMIHOPE LL [3] | 1.00 |
|   | AEROSIL R972 | 3.00 |
|   | TOTAL | 100.00 |

[1] C12-15 alkyl benzoate available from Finetex.
[2] Pentaerythrityl tetraisostearate available from Uniqema.
[3] Lauroyl Lysine powder available from Ajinomoto.

Example 1 was prepared as follows:

The oil of phase A was pre-heated to 100° C. for 10 minutes, with medium mixing, using a propeller mixer.

Phase B (KRATON G1675 M) was added to phase A at 100° C.

Phase B and phase A were mixed at high speed for 30 minutes until phase B was totally dissolved into phase A.

Phase C (Regalite R1100) was then slowly added into phase (A+B) with medium mixing at 95° C. until the solution became homogeneous.

The temperature was reduced to 90° C. and phase D containing oil mixtures was added to phase (A+B+C), and mixed at low speed.

In a separate beaker Phase E ingredients were mixed, by hand, until the pigments were totally wet with oil to form a pigment mixture.

The pigment mixture was then transferred to a three-roll mill and milled until the colors became homogeneous to form a milled pigment mixture.

The milled pigment mixture was then transferred into a beaker containing phase (A+B+C+D) and mixed, at average speed, for approximately 5 minutes.

Phase F was then slowly added into the beaker and mixed for 10 minutes at high speed.

Mixing speed was then reduced and the resulting fluid transferred into individual packages at 90° C.

The samples contained in the packages were then cooled to room temperature.

The samples exhibited desirable shine and wear properties.

Rheology of Example 1

The elastic/storage modulus G', at a frequency of 0.01 rad/s, at a temperature of 25° C., was 26.5 Pa, for the formulation of example 1.

The creep viscosity, at a constant stress of 0.8 Pa, at a temperature of 25° C., was $5.43 \times 10^3$ Pa·s, for the formulation of example 1.

What is claimed is:

1. A cosmetic composition comprising:
   (a) at least one block copolymer having at least one hard segment and at least one soft segment;
   (b) at least one tackifier component comprising a hydrogenated styrene/methyl styrene/indene copolymer;
   (c) at least one solvent capable of solubilizing the at least one hard segment;
   (d) optionally, at least one colorant; and wherein the at least one hard segment has a $T_g$ value of 50° C. or more, and the at least one soft segment has a $T_g$ value of 20° C. or less.

2. The composition of claim 1 wherein (a) has a styrene content of less than about 30% by weight, based on the weight of (a).

3. The composition of claim 1 wherein (a) is present in the composition in an amount of from greater than 0% to about 50% by weight, based on the weight of the composition.

4. The composition of claim 1 wherein (a) is present in the composition in an amount of from greater than 0% to about 10% by weight, based on the weight of the composition.

5. The composition of claim 1 wherein the at least one tackifier component is present in the composition in an amount of from greater than 0% to about 90% by weight, based on the weight of the composition.

6. The composition of claim 1 wherein the at least one tackifier component is present in the composition in an amount of from greater than 0% to about 30% by weight, based on the weight of the composition.

7. The composition of claim 1 wherein the tackifier has a solubility parameter corresponding to δ' and the block copolymer has at least one segment with a solubility parameter corresponding to δ'±2.

8. The composition of claim 1 wherein the at least one solvent capable of solubilizing the at least one hard segment has a viscosity of from about 1 to about 200 cps at room temperature.

9. The composition of claim 1 wherein the at least one solvent capable of solubilizing the at least one hard segment has a viscosity of from about 2 to about 50 cps at room temperature.

10. The composition of claim 1 wherein the at least one solvent capable of solubilizing the at least one hard segment has a solubility parameter corresponding to δ' and block copolymer has at least one hard segment with a solubility parameter corresponding to δ'±2.

11. The composition of claim 1 wherein the at least one solvent capable of solubilizing the at least one hard segment has a solubility parameter corresponding to δ' and the block copolymer has at least one hard segment with a solubility parameter corresponding to δ'±0.7.

12. The composition of claim 1 wherein the at least one solvent capable of solubilizing the at least one hard segment has a weight average molecular weight of from about 100 to about 500.

13. The composition of claim 1 wherein the at least one solvent capable of solubilizing the at least one hard segment further comprises at least one co-solvent having a weight average molecular weight of from about 500 to about 2500.

14. The composition of claim 1 wherein the at least one solvent capable of solubilizing the at least one hard segment is present in the composition in an amount of from greater than 0% to about 85% by weight, based on the weight of the composition.

15. The composition of claim 13 wherein the co-solvent is present in the composition in an amount of from greater than 0% by weight to about 60% by weight, based on the weight of the composition.

16. The composition of claim 1 wherein the at least one solvent capable of solubilizing the at least one hard segment is selected from the group consisting of linear or branched monoesters, diesters, triesters, and mixtures thereof.

17. The composition of claim 1 wherein the colorant is present in an amount effective to impart color when applied onto lips.

18. A process for treating lips comprising contacting the lips with the composition of claim 1.

19. A cosmetic composition comprising:
(a) from about 1 to about 10% by weight of a tri-block thermoplastic elastomer of an A-B-A type copolymer wherein A corresponds to styrene and B corresponds to rubber;
(b) from about 1 to about 40% by weight of at least one hydrogenated hydrocarbon styrene/methyl styrene/indene copolymer;
(c) from about 1 to about 60% by weight of at least one ester of a weight average molecular weight of 100 to 500; and
(d) optionally, at least one colorant;
all weights being based on the weight of the composition.

20. The composition of claim 1 wherein the composition has an elastic/storage modulus G', at a frequency ω of 0.01 rad/s, ranging from about 0.01 Pa to about 500 Pa at 25° C.

21. The composition of claim 19 wherein the composition has an elastic/storage modulus G', at a frequency ω of 0.01 rad/s, ranging from about 0.01 Pa to about 500 Pa at 25° C.

22. The composition of claim 1, wherein the composition has a creep viscosity ($\eta^{creep}$) ranging from about 2 Pa·s to about 150,000 Pa·s, at 25° C.

23. The composition of claim 19, wherein the composition has a creep viscosity ($\eta^{creep}$) ranging from about 2 Pa·s to about 150,000 Pa·s, at 25° C.

24. The composition of claim 1 wherein (a) is a tri-block thermoplastic elastomer of an A-B-A type copolymer wherein A corresponds to styrene and B corresponds to rubber.

25. The composition of claim 1 wherein (a) is a di-block thermoplastic elastomer of an A-B type copolymer wherein A corresponds to styrene and B corresponds to rubber.

26. The composition of claim 1 wherein (a) is a mixture of: (i) at least one di-block thermoplastic elastomer of an A-B type copolymer and (ii) at least one tri-block thermoplastic elastomer of an A-B-A type copolymer, wherein A corresponds to styrene and B corresponds to rubber.

27. The composition of claim 1, wherein (a) comprises a combination of di-block and tri-block copolymers of styrene-ethylene/butylene-styrene.

28. The composition of claim 27, wherein the tackifier is present in an amount of greater than 0 to 30% by weight, based on the weight of the composition.

29. The composition of claim 28, wherein the at least one solvent capable of solubilizing the hard segment is selected from the group consisting of monoesters, diesters, tri-esters, hydrocarbon-based oils of animal origin, hydrocarbon-based oils of plant origin, natural or synthetic esters of the formula $R_1COOR_2$, wherein $R_1$ is a higher fatty acid residue having 7-19 carbon atoms, and $R_2$ is a branched hydrocarbon-based chain having 3-20 carbon atoms, and mixtures thereof.

* * * * *